United States Patent [19]

Sims

[11] 4,432,387

[45] Feb. 21, 1984

[54] ROTATING DISC GATE VALVE

[76] Inventor: Don G. Sims, 4530 Briarhollow, Houston, Tex. 77027

[21] Appl. No.: 420,032

[22] Filed: Sep. 20, 1982

[51] Int. Cl.³ .......................................... F16K 43/00
[52] U.S. Cl. ............................ 137/329.02; 137/330; 251/249.5; 251/302
[58] Field of Search .................... 137/329.02, 329.03, 137/329.04, 330, 454.2; 251/188, 195, 248, 249.5, 302, 327, 328

[56] References Cited

U.S. PATENT DOCUMENTS

| | | | |
|---|---|---|---|
| 695,963 | 3/1902 | Studer | 251/188 |
| 1,456,697 | 5/1923 | Kitts, Jr. | 251/249.5 |
| 1,617,503 | 2/1927 | Seymour et al. | 251/302 |
| 2,812,153 | 11/1957 | Westling | 251/302 |
| 2,977,975 | 4/1961 | Allen | 137/330 |
| 2,977,976 | 4/1961 | Allen | 137/330 |
| 2,977,977 | 4/1961 | Pennington | 137/330 |
| 3,286,980 | 11/1966 | Marshall | 251/302 |
| 3,424,200 | 1/1969 | Marley et al. | 251/302 |

Primary Examiner—George L. Walton
Attorney, Agent, or Firm—Pravel, Gambrell, Hewitt, Kirk & Kimball

[57] ABSTRACT

A rotating disc gate valve for controlling fluid flow in a flow line comprising a valve body having a flow passageway and a cavity transverse to the flow passageway to receive a flow control assembly. The flow control assembly includes first and second valve seat carriers each having a plurality of valve seats thereon which are aligned to form valve seat sets and an independent rotation means for rotating the valve seat carriers whereby replacement valve seats can be axially aligned with the flow passageway without dismantling the valve body. The flow control assembly includes a flow control disc mounted between the valve seat carriers.

17 Claims, 7 Drawing Figures

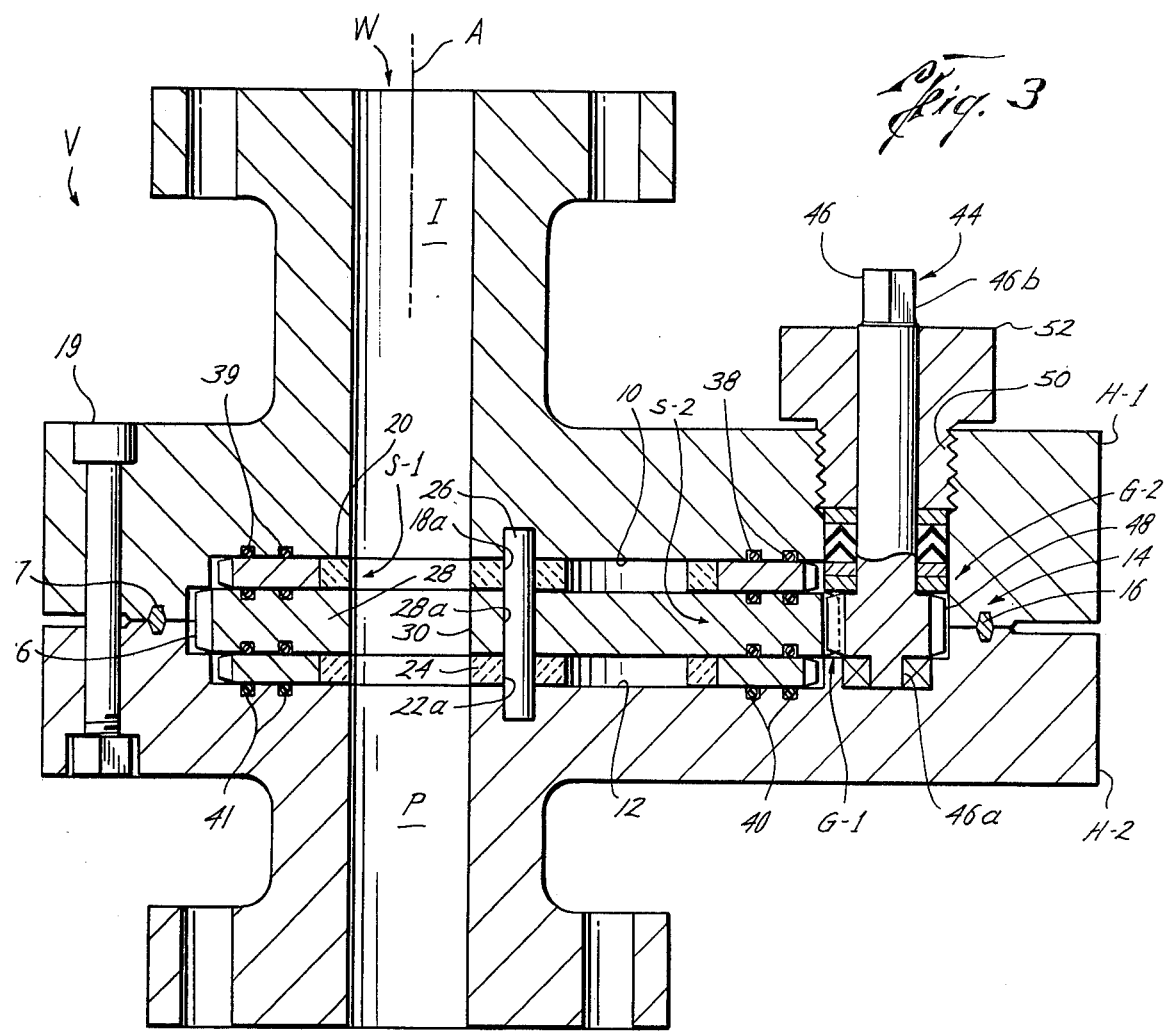
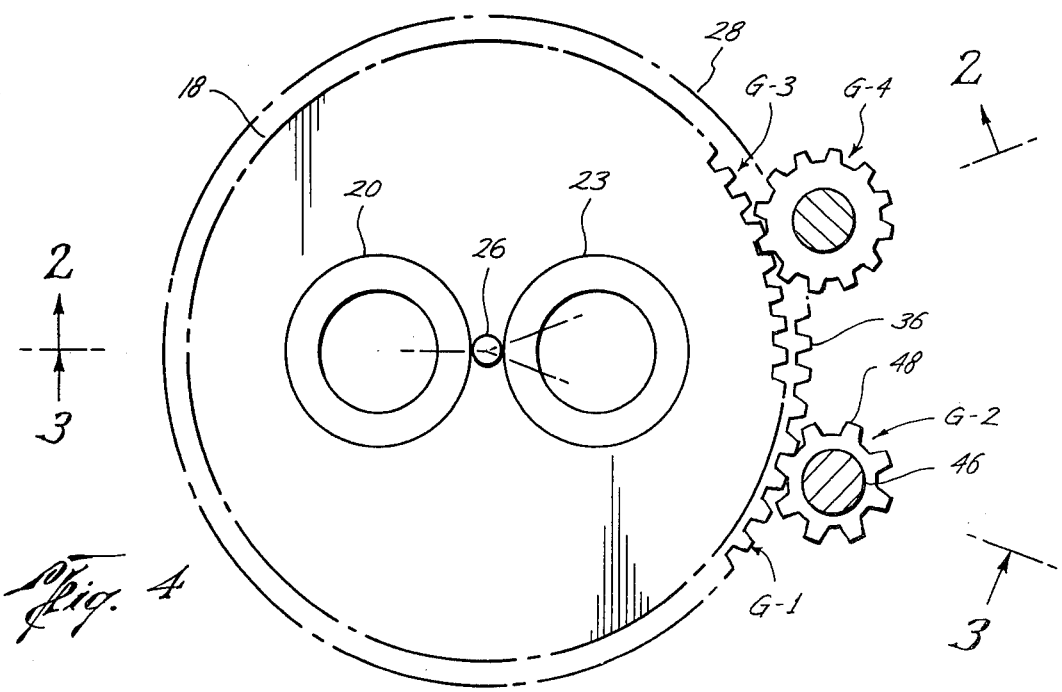

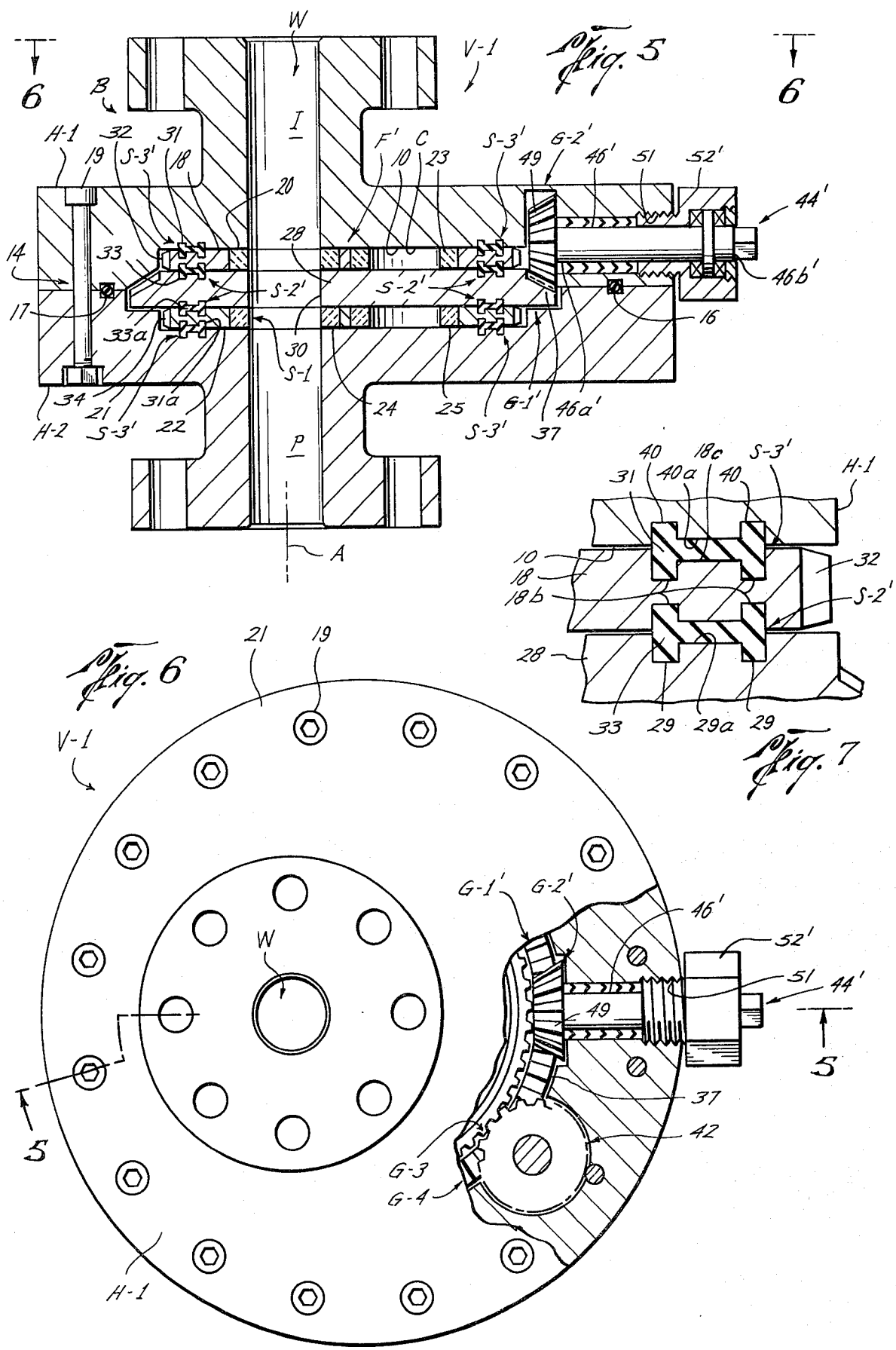

ROTATING DISC GATE VALVE

BACKGROUND OF THE INVENTION

1. Field of the Invention

The field of the present invention is valves for controlling fluid flow in a flow line wherein the valve seats can be replaced without dismantling of the valve body.

2. Prior Art

The use of sliding flow control gates in valves is well known in the prior art. In such a gate valve, the flow control gate is slideably movable to a closed position between valve seats securely mounted in the valve body passageway. Typically such a gate valve has only one set of seats, and when that set of seats failed, it is necessary to dismantle the valve body or remove the valve gate actuator mechanism in order to replace the valve seats.

SUMMARY

A rotating disc gate valve for controlling fluid flow in a flow line comprising a valve body having a flow passageway and a cavity transverse to the passageway for receiving a flow control assembly whereby the flow control assembly can be positioned in opened and closed positions. The flow control assembly includes a first and second valve seat carrier, each having a plurality of valve seats mounted thereon which are alignable to form valve seat sets and a flow control disc rotatably mounted between the first and second valve seat carriers and having a flow control port therein alignable with a valve seat set and the passageway. The flow control assembly also includes independent carrier rotation means for independently rotating the valve seat carriers whereby the valve seat sets are alignable with the passageway. Further, a control disc rotation means rotates the flow control disc to align the flow port with the passageway in an open position.

When the first set of valve seats have become eroded or otherwise incapable of providing a leak resistant seat with the flow control disc, the unused, second set of valve seats may be rotated into axial alignment with the flow passageway without having to dismantle or disassemble the rotating disc gate valve. Since the valve body is split transversly to the flowline, replacement of either the flow control disc or valve seat carriers can be easily accomplished. However, it is anticipated that the operating life of the rotating disc gate valve will be increased over prior art style seated valves due to the availability of the second or replacement valve seat sets.

This summary is not intended to describe all the features of this invention, which are set forth in the description and claims.

DESCRIPTION OF THE DRAWINGS

FIG. 3 is a cross-sectional view of the rotating disc valve taken along line 3—3 of FIG. 4;

FIG. 4 is a section view partly in schematic of the valve seat carrier and flow control disc;

FIG. 5 is a cross-sectional view of a second embodiment of the present invention along the line 5—5 of FIG. 6;

FIG. 6 is a top view and partially cut away view of the second embodiment; and,

FIG. 7 is a detailed section showing retaining rings of the second embodiment between the valve housing and a first valve seat carrier and between the first valve seat carrier and a flow control disc.

DESCRIPTION OF THE PREFERRED EMBODIMENT

Figure 1:
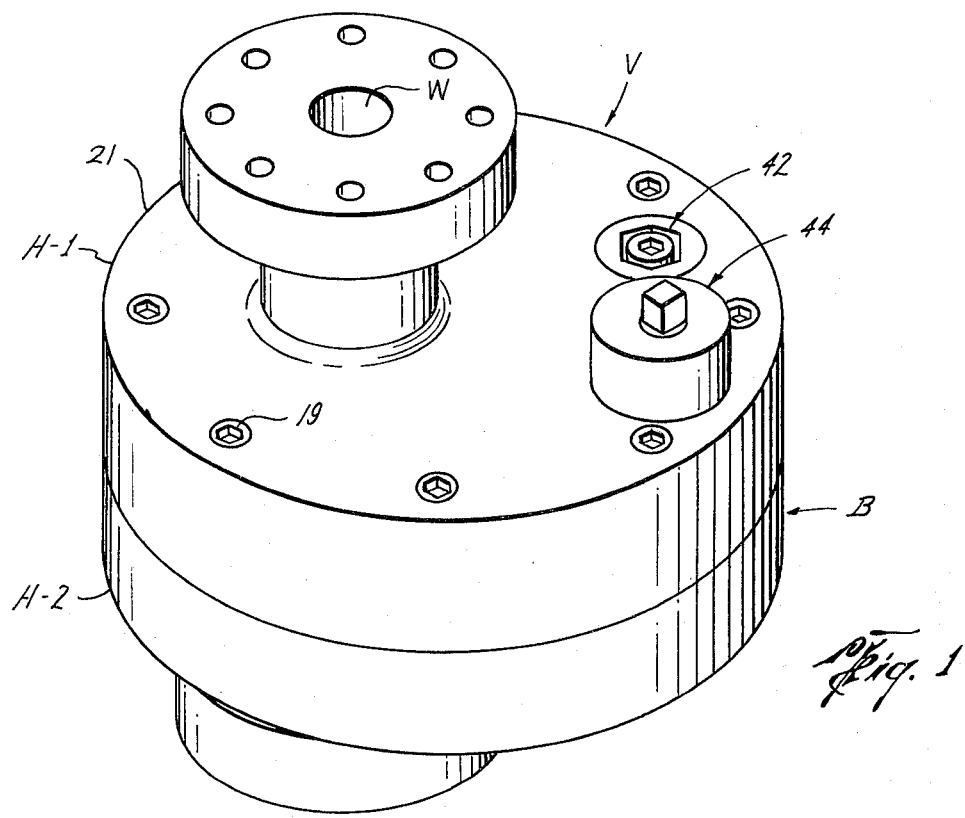
Fig. 1 is an isometric view of the rotating disc valve.

The rotating disc valve of the first embodiment of the present invention, which is illustrated in FIGS. 1–4, is generally designated in the drawings by the letter V. The rotating disc valve V includes a valve body B having formed therein a fluid passageway W and a cavity C extending transversely to said passageway. The second embodiment of the rotating disc valve of this invention is illustrated in FIGS. 5–6 and is generally designated as V-1.

Figure 2:
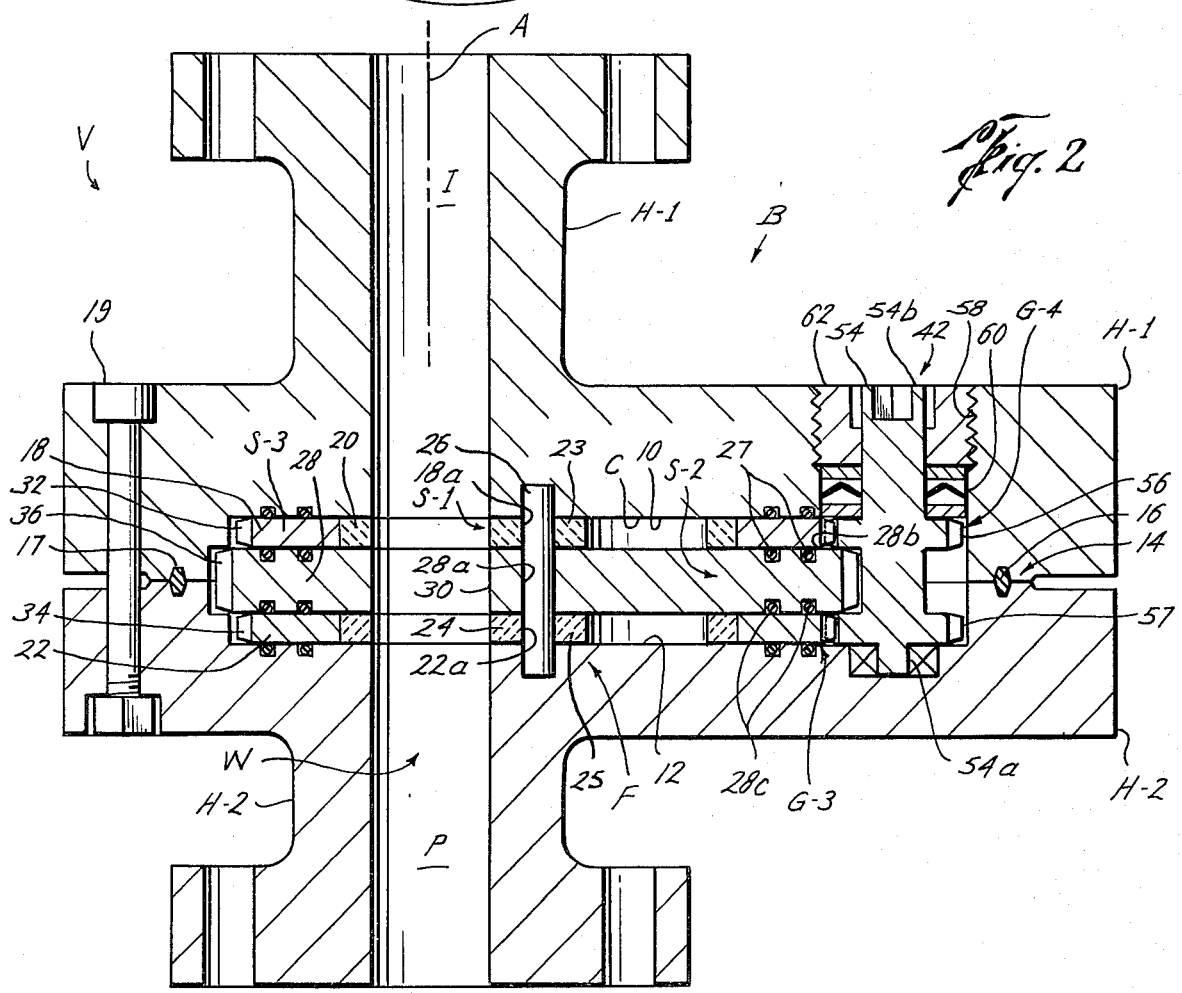
FIG. 2 is a cross-sectional view of the rotating disc valve taken along line 2—2 of FIG. 4.

Referring to FIGS. 1–3, a first embodiment of the present invention includes the valve body B having a first housing H-1 including an inlet passageway I and a surface 10 transverse to the inlet passageway I adapted to receive a flow control assembly F and to sealably mate with a complimentary sealing surface 12 of a second housing H-2. The second housing H-2 has formed therein an outlet passageway P aligned with inlet passageway I with the housings joined together by fastening means 19. The surfaces 10 and 12 cooperate to form the cavity C which receives the flow control assembly F. Each of the housings H-1 and H-2 terminates in flange portions so that the valve V is mountable in a flow line.

The first housing H-1 is sealably mated with second housing H-2 with a suitable sealing means 14 for preventing fluid migration. The suitable sealing means 14 includes a resilient O-ring 16 or any other ring of suitable sealing material mounted in opposing grooves 17 formed in surfaces 10 and 12. The fastening means 19, preferably a nut and bolt arrangement or the like, are uniformly spaced about the periphery 21 of housings H-1 and H-2.

The flow control assembly F is mounted in the valve body cavity C and includes a first valve seat carrier 18 having two annular valve seats 20 and 23 mounted therein, as also shown in FIG. 4, and a second valve seat carrier 22 having two annular valve seats 24 and 25 mounted therein. The carriers 18 and 22 are circular discs each having a diameter smaller than the diameter of the cavity C, which is basically cylindrical in configuration and has an axis parallel to the axis A of the aligned inlet and outlet passageways I and P. The valve seats 20, 23, 24 and 25 are preferably formed from a hard or wear resistant material such as STELLITE or other suitable seat material.

The first and second valve seat carriers 18 and 22 include a central bore 18a and 22a to accept a rotation pin 26. Rotation pin 26 is securely connected to valve body B whereby the valve seat carriers 18 and 22 are mounted for rotation within cavity C of valve body B. Further, the valve seat carriers 18 and 22 have circumferential edges having engageable gear teeth 32 and 34, respectively.

The annular valve seats 20 and 24 aligned with the passageway W, as viewed in FIG. 2 and 3, cooperate to form a set of valve seats 20/24. Similarly, annular valve seats 23 and 25 cooperate to form a set of valve seats 23/25. These valve seat sets 20/24 and 23/25 are alignable with the body passageway W and are sized to effectively prevent fluid escape out of the passageway W in cooperation with valve body B and a flow control disc 28.

The flow control assembly F also includes a flow control disc 28 having formed therein a flow control port 30. The flow control disc 28 is rotatably mounted between the first valve seat carrier 18 and the second valve seat carrier 22. The flow control port 30 of the flow control disc 28 is of a diameter substantially the same as passageways I and P which form combined passageway W. The flow control disc 28 is a predetermined diameter larger than valve seat carriers 18 and 22. The flow control disc 28 further includes a central bore 28a to rotatably accept rotation pin 26 whereby the flow control disc is rotatably mounted between the first and second valve seat carriers 18 and 22. In this manner, both the carrier discs and the flow control disc are mounted for rotation about pin 26, which has an axis offset from but parallel to the axis A of passageway W.

The flow control disc 28 includes engageable gear teeth 36 formed about the periphery of the flow control disc 28 to provide a predetermined angular rotation of the flow control disc 28 between an opened and closed position. In the opened position, the flow port 30 is axially aligned with either valve seat sets 20/24 or 23/25 aligned with passageway W. In the closed position, the flow port 30 is rotated so that no portion of flow port 30 is axially aligned with valve seat set 20/24 or 23/25 aligned with flow passageway W.

The aligned valve seats 20/24 or 23/25 on carriers 18, 22, which are aligned with the passageway W cooperate with rotatable flow control disc 28 and valve body B to provide a first sealing means S-1 positioned circumferentially of the fluid passageway W to prevent the escape of fluid from the passageway W.

A second sealing means, as best seen in FIG. 2, S-2 is mounted circumferentially of the flow control disc 28 for cooperating with the valve seat carriers 18, 22 to prevent the escape of fluid from or out of the valve body cavity C. The second sealing means S-2 includes concentric, annular grooves 28c machined in opposing faces 28b of the disc 28, the grooves having mounted therein O-rings 27 whereby migration of fluid between the valve seat carriers 18, 22 and flow control disc 28 out of valve body cavity C is prevented. The O-rings 27 are positioned circumferentially outwardly of both of said valve seats in each of the valve seat carriers 18 and 22.

A third sealing means, as best seen in FIG. 3, S-3 is mounted circumferentially of the valve body cavity C for cooperating with valve seat carriers 18 and 22 to prevent the escape of fluid from the valve body cavity. The third sealing means S-3 includes two concentric grooves 38 formed in the surface 10 of housing H-1, which forms one side of the cavity C, and having O-rings 39 positioned therein to seal between surface 10 and carrier 18, and concentric grooves 40 machined in surface 12 of housing H-2, which form part of cavity C, and having O-rings 41 positioned therein to seal between surface 12 and carrier 22.

The flow control assembly F further includes a carrier rotation means 42, as seen in FIGS. 1 and 2, mounted with valve body B for rotating and axially aligning the valve seat sets 20/24 and 23/25 with the passageway W and a flow control disc rotation means 44, as seen in FIGS. 1 and 3, mounted with valve body B for rotating the flow control disc 28 between an opened and a closed position.

Referring to FIG. 3, the flow control disc rotation means 44 mounted with valve body B includes the rotation pin 26 securely mounted in valve housings H-1, H-2 and engaging central bore 28a of the flow control disc 28. The flow control disc rotation means 44 further includes peripheral gear ring 36 on disc 28 as a first gear means G-1 and a second gear means G-2 extending from outside of the valve body B into engagement with the first gear means G-1 whereby rotation of the second gear means rotates the first gear means G-1 and the flow control disc 28.

The second gear means G-2 includes a flow disc operator or actuator shaft 46 having gear teeth 48 engageable with the gear teeth 36 of flow control disc 28. Rotation of flow disc operator 46 rotates the flow control disc 28 between the opened and closed position.

The flow disc operator 46 is a shaft having a lower end 46a journaled with housing H-2 and an upper end 46b extending through partially threaded bore 50 of housing H-1 and adapted to receive a valve hand wheel (not shown) or the like. The valve operator 46 has engageable gear teeth 48 formed thereon to engage gear teeth 36 of flow control disc 28. The operator 46 is mounted for rotation by a suitable combination of bearings, packing and a retainer nut 52 and rotates about an axis parallel to the axis A of passageway W.

Referring to FIG. 2, carrier rotation means 42 is mounted with the valve body B and includes the rotation pin 26 securely mounted in valve housings H-1 and H-2 and engaging the central bores 18a, 22a of valve seat carriers 18, 22. The carrier rotation means 42 further includes a third gear means G-3 mounted with valve seat carriers 18, 22 and a fourth gear means G-4 extending from outside of valve body B into engagement with the third gear means G-3 whereby rotation of the fourth gear means G-4 rotates the third gear means and valve seat carriers 18, 22. The third gear means G-3 includes engageable gear teeth 32 and 34 formed on valve seat carriers 18 and 22, respectively, at the circumferential surface or periphery thereof. The fourth gear means G-4 includes a valve carrier operator 54 which is a shaft having a pair of spaced gear teeth 56 and 57 engageable with the gear teeth 32 and 34, respectively, of the valve seat carriers 18 and 22. Rotation of valve seat carrier operator 54 rotates the first and second valve seat carriers 18 and 22 so that either of the valve seat sets 21/24 or 20/25 are axially alignable with the passageway P. Valve seat carrier operator 54 further retains the valve seat sets in axial alignment with the passageway W.

The shaft of valve seat carrier operator 54 has a lower end 54a journaled with the valve housing H-2 and an upper end 54b extending into a partially threaded bore 58 of housing H-1. The shaft of operator 54 is flush mounted with the valve body B and adapted at the upper end 54b to receive an "Allen" wrench or the like. A packing ring 60 and retainer nut 62 secure the position of the shaft for rotation about an axis parallel to the axis A of the passageway W.

The rotating disc gate valve V of the present invention may be operated to control the fluid flow in a flow line (not shown) whereby the flow control port 30 is axially aligned with the valve seat set 20/24 and passageway W in the opened position or flow control disc 28 is positioned so that no part of flow control disc 28 is positioned so that no part of flow control port 30 is axially aligned with the valve seat set 20/24 and passageway W in the closed position.

After valve seats 20/24 have become eroded or otherwise incapable of providing a leak resistant seat with flow control disc 28, unused, replacement valve seats 23/25, may be rotated into axial alignment with passageway W without having to dismantle or disassemble the rotating disc valve V. The sealing means S-1, S-2 and S-3, limit the exposure of the operators 54 and 46 to the possibly corrosive environment of the fluid in the flow line. The aligned valve seats such as 20/24 serve as a first barrier to escape of fluid from passageway W. When the valve seat set 20/24 becomes worn and when the set 20/24 is being replaced by set 23/25, the sealing means S-1, S-2 and S-3, on both sides of flow control disc 28 cooperate to prevent the escape of fluid from chamber cavity C.

Since the valve body B is split transversely to the flow line, replacement of either the flow control disc or valve seat carriers can be easily accomplished if necessary, but it is anticipated that the operating life of the rotating disc gate valve prior to disassembly will be increased over prior art single seated valves due to the availability of the alternate valve seat sets.

Looking now at FIGS. 5 and 6, the same numbers in the first embodiment will be used to describe essentially the same parts in this second embodiment. The second embodiment of the present invention generally indicated by the letter V-1, includes a valve body B having a first housing H-1 including an inlet passageway I and a surface 10 transverse to the inlet passageway I adapted to receive a flow control assembly F' and to sealably mate with a complimentary sealing surface 12 of a second housing H-2. The second housing H-2 has formed therein an outlet passageway P aligned with inlet passageway I with the housings joined together by fastening means 19. The surfaces 10 and 12 cooperate to form the cavity C which receives the flow control assembly F'. Each of the housings H-1 and H-2 terminate in flange portions so that the valve V-1 is mountable in a flow line.

The first housing H-1 is sealably mated with the second housing H-2 with a suitable sealing means 14 for preventing fluid migration. The suitable sealing means 14 includes a resilient O-ring 16 or any other ring of suitable sealing material mounted in opposing grooves 17 formed in surfaces 10 and 12. The fastening means 19, preferably a nut and bolt arrangement or the like, are uniformly spaced about the periphery 21 of housings H-1 and H-2.

The flow control assembly F' is mounted in the valve body cavity C and includes a first valve seat carrier 18 having two annular valve seats 20 and 23 mounted therein, as also shown in FIG. 4, and a second valve seat carrier 22 having two annular valve seats 24 and 25 mounted therein. The carriers 18 and 22 are circular discs each having a diameter smaller than the diameter of the cavity C, which is basically cylindrical in configuration and has an axis parallel to the axis A of the aligned inlet and outlet passageways I and P. The valve seats 20 and 23 and 24 and 25 are preferably formed from a hard or wear resistant material such as STELLITE or other suitable seat material.

Looking now at FIGS. 5 and 7, the first valve seat carrier 18 includes a pair of concentric annular grooves 18b on both planar surfaces thereof. The grooves 18b are joined by a recessed portion 18c. The surface 10 of housing H-1 contains opposing and complimentary pair of concentric annular grooves 40. The grooves 40 are joined by a recessed portion 40a. Similarly, flow disc 28 includes a pair of concentric annular grooves 29 on both planar surfaces thereof. The grooves 29 are joined by a recessed portion 29a.

A first retainer ring 31, having an H-shaped cross-section, is adapted to slidably engage opposing complimentary annular grooves 40 and 18b, as best seen in FIG. 7. Such first retainer ring 31 is preferably made from TEFLON or the like and is adapted to retain the axial alignment of valve seat carrier 18 within valve housing H-1. A second retaining ring 33 is mounted between the carrier disc 18 and flow control disc 28 in grooves 18b and 29 with interconnecting recesses. Similarly, retainer rings 33a and 31a are mounted in grooves in between flow control disc 28 and valve seat carrier 22, and the valve seat carrier 22 and housing H-2, respectively.

The retainer rings 31/33 and 31a/33a permit valve seat carriers 18, 22 and flow control disc 28 to slidably rotate about an axis which is parallel to but offset from axis A of passageway W within cavity C of valve body B. Further, the valve seat carriers 18 and 22 have circumferential edges having engageable gear teeth 32 and 34, respectively, formed thereon about the circumference of the valve seat carriers.

The annular valve seats 20 and 24 which are aligned with the passageway W as viewed in FIG. 5, cooperate to form a set of valve seats 20/24. Similarly, annular valve seats 23 and 25 cooperate to form a set of valve seats 23/25. These valve seat sets 20/24 and 23/25 are alignable with the body passageway W and are sized to effectively prevent fluid escape out of the passageway W in cooperation with valve body B and a flow control disc 28.

The flow control assembly F' also includes the flow control disc 28 having formed therein a flow control port 30. The flow control disc 28 is rotatably mounted between the first valve seat carrier 18 and the second valve seat carrier 22. The flow control port 30 of the flow control disc 28 is of a diameter substantially the same as passageways I and P which form combined passageway W. The flow control disc 28 is a predetermined diameter larger than valve seat carriers 18 and 22.

The retainer rings 33 and 33a are positioned in engagement with spaced concentric grooves such as 29 shown on the face of flow control disc 28 and with grooves in the carrier discs 18 and 22 in order to mount the flow control disc 28 for rotation.

The retainer rings 31 and 31a are positioned in engagement with spaced concentric grooves such as 40 on surface 10 of housing H-1 or surface 12 of housing H-2 and with grooves in carrier discs 18 and 22 in order to mount the valve seat carriers 18 and 22 for rotation.

The flow control disc 28 also includes engageable bevel gear teeth 37 formed about the periphery of the flow control disc 28 to provide a predetermined angular rotation of the flow control disc 28 between an opened and closed position. In the opened position, the flow port 30 is axially aligned with either valve seat sets 20/24 or 23/25 aligned with passageway W. In the closed position, the flow port 30 is rotated so that no portion of flow port 30 is axially aligned with valve seat set 20/24 or 23/25 aligned with flow passageway W.

The aligned valve seats 20/24 or 23/25 on carriers 18, 22, which are aligned with the passageway W cooperate with rotatable flow control disc 28 and valve body B to provide a first sealing means S-1 positioned circumferentially of the fluid passageway W to prevent the escape of fluid from the passageway W, as best seen in FIG. 5.

Looking now at FIGS. 5 and 7, a second sealing means S-2' is mounted circumferentially of the flow control disc 28 for cooperating with the valve seat carriers 18, 22 to prevent the escape of fluid from or out of the valve body cavity C. The second sealing means S-2' includes retainer rings 33 and 33a whereby migration of fluid between the valve seat carriers 18, 22 and flow control disc 28 out of valve body cavity C is prevented. The retainer rings 33 and 33a are positioned circumferentially outwardly of both of said valve seats in each of the valve seat carriers 18 and 22.

A third sealing means S-3' is mounted circumferentially of the valve body cavity C for cooperating with valve seat carriers 18 and 22 to prevent the escape of fluid from the valve body cavity, as best seen in FIG. 7. The third sealing means S-3' includes retainer ring 31 positioned therein to seal between surface 10 and carrier 18 and ring 31a positioned between carrier 22 and housing surface 12.

The flow control assembly F' further includes a carrier rotation means 42 mounted with valve body B for rotating discs 18 and 22 and axially aligning the valve seat sets 20/24 and 23/25 with the passageway W and a flow control disc rotation means 44' mounted with valve body B for rotating the flow control disc 28 between an opened and a closed position.

Referring to FIG. 5, the flow control disc rotation means 44' mounted with valve body B includes the retainer rings 33 and 33a slidably mounted between the valve seat carriers 18, 22 and flow control disc 28. The flow control disc rotation means 44' further includes a peripheral bevel gear ring 37 on disc 28 as a first gear means G-1' and a second gear means G-2' extending from outside of the valve body B into engagement with the first gear means G-1' whereby rotation of the second gear means rotates the first gear means G-1' and the flow control disc 28. The second gear means G-2' includes a flow disc operator or actuator shaft 46' having bevel gear teeth 49 engageable with the gear teeth 37 of flow control disc 28. Rotation of flow disc operator 46' rotates the flow control disc 28 between the opened and closed position.

The flow disc operator 46' is a shaft having a lower end 46a' journaled with housing H-1 and an upper end 46b' extending through partially threaded bore 51 of housing H-1 and adapted to receive a valve hand wheel (not shown) or the like. The valve operator 46' has engageable bevel gear teeth 49 formed thereon to engage bevel gear teeth 37 of flow control disc 28. The operator 46' is mounted for rotation by a suitable combination of bearings, packing and a retainer nut 52' and rotates about an axis perpendicular to the axis A of passageway W.

As in the first embodiment in FIG. 2, the carrier rotation means 42 of the second embodiment V-1 is mounted with the valve body B and includes the retainer rings 31 and 31a. The carrier rotation means 42 further includes a third gear means G-3 mounted with valve seat carriers 18, 22 in the same manner as the first embodiment. The fourth gear means G-4 is identical, except the size of the gears, to that of the fourth gear means of FIG. 1.

The foregoing disclosure and description of the invention are illustrative and explanatory thereof, and various changes in the size, shape and materials as well as in the details of the illustrated construction may be made without departing from the spirit of the invention. For example, the valve seat carriers 18, 22 as shown in FIGS. 2, 3 contain pairs of valve seats 20/23, 24/25 although as is understood by one skilled in the art a multiplicity of said valve seats may be mounted on the valve seat carriers 18, 22 whereby a multiplicity of valve seat sets could be formed.

I claim:

1. A rotating disc gate valve for controlling fluid flow in a flow line, comprising:
   a valve body having formed therein a fluid passageway and a cavity extending transversely to said passageway; and,
   a flow control assembly mounted with said valve body cavity, including:
     first and second valve seat carriers mounted within said valve body cavity, said valve seat carriers each having a plurality of valve seats which are alignable with valve seats in the other valve seat carrier to form valve seat sets, said valve seat sets are alignable with said passageway;
     carrier rotation means mounted with said valve body for rotating said valve seat carriers to a plurality of positions in which one of said valve seat sets are aligned with said passageway;
     a rotatable flow control disc having formed therein a flow control port alignable with said valve seat sets;
     flow control disc rotation means mounted with said valve body for rotating said flow control disc between an opened and closed position, said flow control port of said flow control disc being simultaneously aligned with said valve seat sets and said fluid passageway in the opened position; and
     said sets of seats of said valve seat carriers providing the rotating disc valve with multiple sets of seats whereby said valve seat set alignable with said valve body passageway is replaceable without dismantling of said valve body.

2. The rotating disc gate valve of claim 1, wherein said valve body includes:
   a first housing having formed therein a fluid flow inlet passageway;
   a second housing having formed therein a flow outlet passageway;
   fastening means mounting said first and second housings together with said flow inlet and outlet passageways being aligned; and
   said first and second housings cooperating to form said cavity in which said flow control assembly is mounted.

3. The rotating disc gate valve of claim 1, wherein said flow control disc rotation means includes:
   engageable gear teeth formed on the periphery of said flow control disc;
   a pin mounted within said valve body cavity, said flow control disc being mounted for rotation by said pin; and
   a flow control disc operator shaft being mounted with said valve body and having formed thereon gear teeth engageable with said flow control disc gear teeth whereby rotation of said disc operator shaft rotates said flow control disc.

4. The rotating disc gate valve of claim 1 or 3, wherein said carrier rotation means includes:
   engageable gear teeth formed on the periphery of said valve seat carriers;

a pin mounted within said valve body cavity, said valve seat carriers being mounted for rotation by said pin; and, a valve carrier operator mounted with said valve body and having formed thereon gear teeth engageable with said valve seat carrier gear teeth whereby rotation of said valve seat operator rotates said valve seat carriers.

5. The rotating disc gate valve of claim 1, wherein:
said valve seat carriers are positioned in a plane transverse to said passageway.

6. The rotating disc gate valve of claim 5, wherein:
said flow control disc is positioned in a plane transverse to said passageway.

7. The rotating disc gate valve of claim 3, wherein:
said flow control disc operator shaft extends through said first housing into said cavity, said actuator shaft including a portion accessible from outside of said first or second housings for rotating said shaft.

8. The rotating disc gate valve of claim 1, wherein said flow control disc rotation means includes:
first gear means mounted with said rotatable flow control disc and second gear means extending from outside of said valve body into engagement with said first gear means whereby rotation of said second gear means rotates said first gear means and said rotatable flow control disc.

9. The rotating disc gate valve of claim 1 or 8, wherein said carrier rotation means includes:
third gear means mounted with said valve seat carrier and fourth gear means extending from outside of said valve body into engagement with said third gear means for rotation of said valve seat carriers whereby rotation of said fourth gear means causes rotation of said third gear means mounted with said valve seat carriers.

10. The rotating disc gate valve of claim 1, wherein:
said valve seat carriers and said rotatable flow control disc are rotated about a common axis which is offset from but parallel to the axis of said passageway.

11. The rotating disc gate valve of claim 1, wherein:
each of said valve seat sets in said valve seat carriers, cooperating with said rotatable flow control disc and valve body to provide a first sealing means positioned circumferentially of said valve body fluid passageway with one of said sets being aligned with said passageway.

12. The rotating disc gate valve of claim 11, wherein:
said flow control disc includes a second sealing means mounted circumferentially of said flow control disc for cooperating with said valve seat carriers to prevent the escape of fluid out of said valve body cavity, said second sealing means being mounted with said flow control disc and being positioned circumferentially about both of said valve seats in each of said first and second valve seat carriers.

13. The rotating disc gate valve of claim 12, wherein:
said valve body includes a third sealing means mounted circumferentially of said valve body cavity for cooperation with said valve seat carriers to prevent the escape of fluid out of said valve body cavity, said third sealing means being mounted in said valve body and positioned circumferentially about both of said valve seats in each of said first and second valve seat carriers.

14. The rotating disc gate valve of claim 1, wherein said flow control disc rotation means includes:
engageable gear teeth formed on the periphery of said flow control disc;
first retainer rings mounted between said valve seat carriers and said flow control disc for axial alignment and rotation of said flow control disc relative to said valve seat carriers; and
a flow control disc operator shaft being mounted with said valve body and having formed thereon gear teeth engageable with said flow control disc gear teeth whereby rotation of said disc operator shaft rotates said flow control disc.

15. The rotating disc gate valve of claim 1 or 14, wherein said carrier rotation means includes:
engageable gear teeth formed on the periphery of said valve seat carriers;
retainer rings slidably mounted between said valve seat carriers and said valve body for axial alignment and rotation of said valve seat carriers relative to said valve body and said flow control disc; and,
a valve carrier operator mounted with said valve body and having formed thereon gear teeth engageable with said valve seat carrier gear teeth whereby rotation of said valve seat operator independently rotates said valve seat carriers.

16. The rotating disc gate valve of claim 3 or 14, wherein said flow control disc operator shaft includes:
means for mounting said control disc operator shaft parallel to the axis of said flow passageway.

17. The rotating disc gate valve of claim 3 or 14, wherein said flow control disc operator shaft includes:
means for mounting said control disc operator shaft perpendicular to the axis of said flow passageway.

* * * * *